(12) United States Patent
Woollam

(10) Patent No.: US 9,226,896 B2
(45) Date of Patent: *Jan. 5, 2016

(54) CRYSTALLINE FREEBASE FORMS OF A BIPHENYL COMPOUND

(71) Applicant: Grahame Woollam, Basel (CH)

(72) Inventor: Grahame Woollam, Basel (CH)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/547,455

(22) Filed: Nov. 19, 2014

(65) Prior Publication Data

US 2015/0164796 A1 Jun. 18, 2015

Related U.S. Application Data

(60) Continuation of application No. 13/973,174, filed on Aug. 22, 2013, now Pat. No. 8,921,396, which is a division of application No. 12/835,964, filed on Jul. 14, 2010, now Pat. No. 8,541,451.

(60) Provisional application No. 61/225,803, filed on Jul. 15, 2009.

(51) Int. Cl.
| | |
|---|---|
| A61K 9/12 | (2006.01) |
| C07D 401/12 | (2006.01) |
| C07D 211/62 | (2006.01) |
| A61K 31/4545 | (2006.01) |
| A61K 45/06 | (2006.01) |

(52) U.S. Cl.
CPC ............ *A61K 9/124* (2013.01); *A61K 31/4545* (2013.01); *A61K 45/06* (2013.01); *C07D 211/62* (2013.01); *C07D 401/12* (2013.01); *C07B 2200/13* (2013.01)

(58) Field of Classification Search
CPC .. C07D 211/06; C07D 211/62; C07D 401/12; A61K 31/4545; A61K 45/06; A61K 9/124; C07B 2200/13

See application file for complete search history.

(56) References Cited

U.S. PATENT DOCUMENTS

| | | | |
|---|---|---|---|
| 3,903,137 | A | 9/1975 | Miura et al. |
| 6,693,202 | B1 | 2/2004 | Aggen et al. |
| 7,524,880 | B2 | 4/2009 | Li et al. |
| 7,700,777 | B2 | 4/2010 | Axt et al. |
| 8,242,137 | B2 | 8/2012 | Axt et al. |
| 8,377,965 | B2 | 2/2013 | Axt et al. |
| 8,716,313 | B2 | 5/2014 | Axt et al. |
| 2003/0018019 | A1 | 1/2003 | Meade et al. |
| 2005/0113413 | A1 | 5/2005 | Wilson et al. |
| 2005/0203133 | A1 | 9/2005 | Mammen et al. |
| 2006/0205949 | A1 | 9/2006 | Dalziel et al. |
| 2007/0112027 | A1 | 5/2007 | Axt et al. |
| 2010/0048622 | A1 | 2/2010 | Axt et al. |

FOREIGN PATENT DOCUMENTS

EP 0747355 A1 12/1996

OTHER PUBLICATIONS

Caira, M.R., "Crystalline Polymorphism of Organic Compounds", Topics in Current Chemistry, vol. 198, pp. 163-208 (1998).
International Search Report for PCT/US2010/041903 dated Sep. 1, 2010.
Naito et al., "Selective Muscarinic Antagonist. II. 1) Synthesis and Antimuscarinic Properties of Biphenylylcarbannate Derivatives", Chem. Pharm. Bull., vol. 46, No. 8, pp. 1286-1294 (1998).

*Primary Examiner* — Sarah Pihonak
(74) *Attorney, Agent, or Firm* — Jeffrey A. Hagenah

(57) ABSTRACT

The invention provides two crystalline freebase forms of biphenyl-2-ylcarbamic acid 1-(2-{[4-(4-carbamoylpiperidin-1-ylmethyl)benzoyl]methylamino}ethyl)piperidin-4-yl ester. The invention also provides pharmaceutical compositions comprising the crystalline freebase or prepared using the crystalline freebases; processes and intermediates for preparing the crystalline freebases; and methods of using the crystalline freebases to treat a pulmonary disorder.

17 Claims, 4 Drawing Sheets

CRYSTALLINE FREEBASE FORMS OF A BIPHENYL COMPOUND

CROSS-REFERENCE TO RELATED APPLICATIONS

This application is a continuation application of U.S. Ser. No. 13/973,174, filed Aug. 22, 2013, now allowed; which is a divisional application of U.S. Ser. No. 12/835,964, filed Jul. 14, 2010, now U.S. Pat. No. 8,541,451; which claims the benefit of U.S. Provisional Application No. 61/225,803, filed on Jul. 15, 2009; the entire disclosures of which are incorporated herein by reference.

BACKGROUND OF THE INVENTION

1. Field of the Invention

The present invention relates to novel crystalline forms of a biphenyl compound, which are expected to be useful for treating pulmonary disorders. The invention also relates to pharmaceutical compositions comprising the crystalline compounds or prepared from such compounds, processes and intermediates for preparing such crystalline compounds and methods of using such compounds to treat a pulmonary disorder.

2. State of the Art

U.S. Patent Publication No. 2005/0203133 to Mammen et al. discloses novel biphenyl compounds that are expected to be useful for treating pulmonary disorders such as chronic obstructive pulmonary disease (COPD) and asthma. In particular, the compound biphenyl-2-ylcarbamic acid 1-(2-{[4-(4-carbamoylpiperidin-1-ylmethyl) benzoyl]methylamino}ethyl)piperidin-4-yl ester is specifically described in this application as possessing muscarinic receptor antagonist or anticholinergic activity.

The chemical structure of biphenyl-2-ylcarbamic acid 1-(2-{[4-(4-carbamoyl piperidin-1-ylmethyl)benzoyl]methylamino}ethyl)piperidin-4-yl ester is represented by formula I:

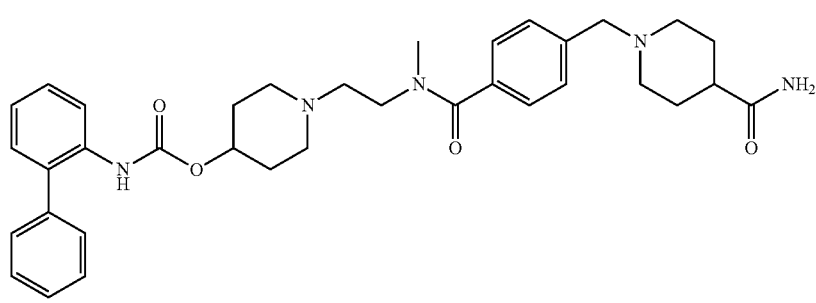

I

The compound of formula I has been named using the commercially-available AutoNom software (MDL, San Leandro, Calif.).

Therapeutic agents useful for treating pulmonary or respiratory disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point thereby allowing the material to be micronized without significant decomposition. Although crystalline freebase forms of the compound of formula I have been reported in U.S. Patent Publication No. 2007/0112027 to Axt et al. as Form I and Form II, the crystalline freebase forms of the present invention have different and particularly useful properties, including higher melting points.

SUMMARY OF THE INVENTION

One aspect of the invention relates to crystalline freebase forms of biphenyl-2-ylcarbamic acid 1-(2-{[4-(4-carbamoylpiperidin-1-ylmethyl)benzoyl]methylamino}ethyl) piperidin-4-yl ester characterized by a powder x-ray diffraction pattern comprising diffraction peaks at 2θ values of 6.6±0.1, 13.1±0.1, 18.6±0.1, 19.7±0.1, and 20.2±0.1.

Another aspect of the invention relates to a crystalline freebase of biphenyl-2-ylcarbamic acid 1-(2-{[4-(4-carbamoylpiperidin-1-ylmethyl)benzoyl]methylamino}ethyl) piperidin-4-yl ester, designated as form III, which is characterized by a powder x-ray diffraction pattern comprising diffraction peaks at 2θ values of 6.6±0.1, 13.1±0.1, 18.6±0.1, 19.7±0.1, and 20.2±0.1; and further characterized by having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1.

Still another aspect of the invention relates to a crystalline freebase of biphenyl-2-ylcarbamic acid 1-(2-{[4-(4-carbamoylpiperidin-1-ylmethyl)benzoyl]methylamino}ethyl) piperidin-4-yl ester, designated as form IV, which is characterized by a powder x-ray diffraction pattern comprising diffraction peaks at 2θ values of 6.6±0.1, 13.1±0.1, 18.6±0.1, 19.7±0.1, and 20.2±0.1; and further characterized by having five or more additional diffraction peaks at 2θ values selected from 10.6±0.1, 15.0±0.1, 16.0±0.1, 17.3±0.1, 17.7±0.1, 20.9±0.1, 21.4±0.1, 22.6±0.1, 24.6±0.1, and 27.8±0.1.

Another aspect of the invention relates to pharmaceutical composition comprising a crystalline freebase of the invention and a pharmaceutically acceptable carrier. Yet another aspect of the invention relates to pharmaceutical compositions comprising a crystalline freebase of the invention in combination with one or more other therapeutic agents. Accordingly, in one embodiment, the invention relates to a pharmaceutical composition comprising (a) a pharmaceutically acceptable carrier and a therapeutically effective amount of a crystalline freebase of the invention; and (b) a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the crystalline freebase and the agent are formulated together or separately. When the agent is formulated separately, a pharmaceutically acceptable carrier may be included. Typically, the crystalline freebase of the invention and the agent will be present in therapeutically effective amounts.

Another aspect of the invention relates to a pharmaceutical composition comprising an aqueous isotonic saline solution comprising a crystalline freebase of the invention, wherein the solution has a pH in the range of from about 4 to 6. In a particular embodiment, an aqueous nebulizer formulation is buffered with citrate buffer to a pH of about 5.

In one embodiment, this invention relates to a drug delivery device comprising a dry powder inhaler containing a pharmaceutical composition comprising a pharmaceutically acceptable carrier and a crystalline freebase of the invention.

The compound of formula I has muscarinic receptor antagonist activity. Accordingly, a crystalline freebase of the compound of formula I is expected to have the same activity, and thus find utility in treating pulmonary disorders such as asthma and chronic obstructive pulmonary disease. Thus, another aspect of the invention relates to a method for treating a pulmonary disorder comprising administering to a patient a therapeutically effective amount of a crystalline freebase of the invention. Still another aspect of the invention relates to a method of producing bronchodilation in a patient comprising administering to the patient a bronchodilation-producing amount of a crystalline freebase of the invention. In one embodiment, the compound is administered by inhalation. The invention also provides a method of treating chronic obstructive pulmonary disease or asthma comprising administering to a patient a therapeutically effective amount of a crystalline freebase of the invention. Another aspect of the invention relates to a method for antagonizing a muscarinic receptor in a mammal comprising administering to the mammal a therapeutically effective amount of a crystalline freebase of the invention.

The invention also relates to processes for preparing crystalline freebase forms of the compound of formula I. The invention also provides a process for purifying the compound of formula I comprising forming a crystalline freebase of biphenyl-2-ylcarbamic acid 1-(2-{[4-(4-carbamoylpiperidin-1-ylmethyl)benzoyl]methylamino}ethyl) piperidin-4-yl ester. The invention further relates to products prepared by the processes described herein.

The invention also relates to a crystalline freebase of the compound of formula I in a micronized form; and to pharmaceutical compositions comprising a pharmaceutically acceptable carrier and a micronized crystalline freebase of the invention.

The invention also relates to crystalline freebase forms of the compound of formula I for use in therapy or as a medicament. Additionally, the invention relates to use of a crystalline freebase of the invention for the manufacture of a medicament; especially for the manufacture of a medicament for the treatment of a pulmonary disorder or for antagonizing a muscarinic receptor in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
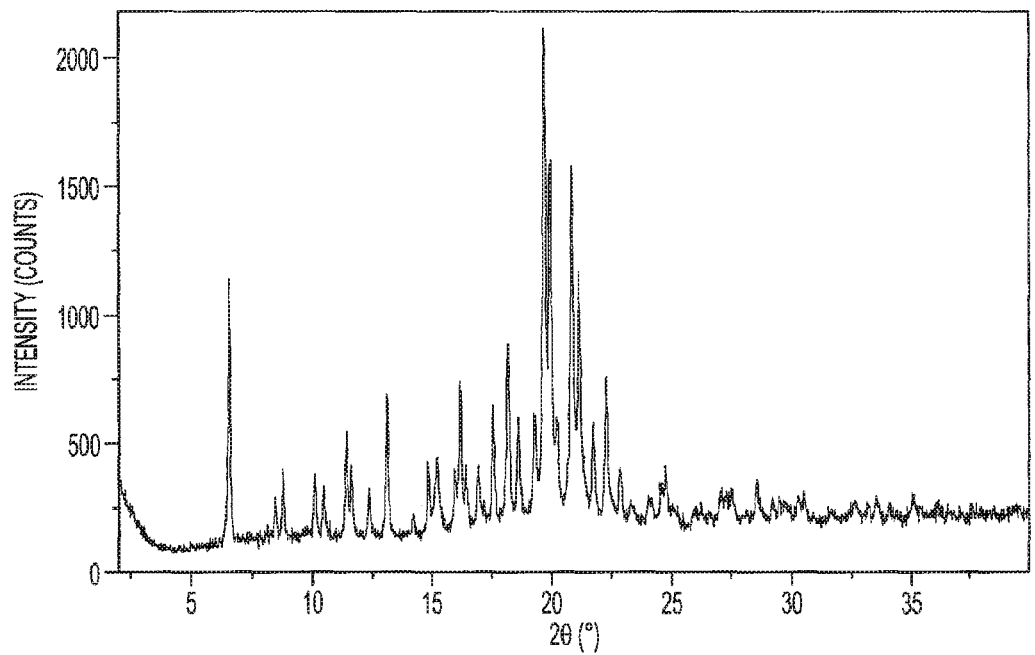
FIG. 1 shows a powder x-ray diffraction (PXRD) pattern of Form III of the crystalline freebase of biphenyl-2-ylcarbamic acid 1-(2-{[4-(4-carbamoylpiperidin-1-ylmethyl)benzoyl] methylamino}ethyl)piperidin-4-yl ester (the compound of formula I). Other characteristics of Form III are presented in FIG. 4, which shows a differential scanning calorimetry (DSC) thermogram and FIG. 6, which shows a thermal gravimetric analysis (TGA) trace.

The present invention provides crystalline freebase forms of biphenyl-2-ylcarbamic acid 1-(2-{[4-(4-carbamoylpiperidin-1-ylmethyl)benzoyl]methylamino}ethyl)piperidin-4-yl ester (formula I). Surprisingly, the crystalline freebase forms of the invention have been found not to be deliquescent, even when exposed to atmospheric moisture. Additionally, the crystalline freebase forms of the invention have acceptable levels of hygroscopicity and acceptable melting points. For example, the crystalline freebase Form III has a melting point of about 125° C. and the crystalline freebase Form IV has a melting point of about 119° C.

Among other uses, the crystalline freebase forms of the invention are useful for preparing pharmaceutical compositions expected to have utility in treating pulmonary disorders. Accordingly, one aspect of the invention relates to a pharmaceutical composition comprising a pharmaceutically acceptable carrier and a therapeutically effective amount of a crystalline freebase of the invention.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

Both Form III and Form IV are anhydrous freebase crystal polymorphs. When reference is made to "a crystalline freebase of the invention", it is understood that the term includes Form III and Form IV.

As used herein, the phrase "having the formula" or "having the structure" is not intended to be limiting and is used in the same way that the term "comprising" is commonly used.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating a pulmonary disorder is an amount of compound needed to, for example, reduce, suppress, eliminate or prevent the symptoms of asthma or chronic obstructive pulmonary disease ("COPD"), or to treat the underlying cause of asthma or COPD. In one embodiment, a therapeutically effective amount is that amount needed to produce bronchodilation. On the other hand, the term "effective amount" means an amount sufficient to obtain a desired result, which may not necessarily be a therapeutic result. For example, when studying a system comprising a muscarinic receptor, an "effective amount" may be the amount needed to antagonize the receptor.

The term "treating" or "treatment" as used herein means the treating or treatment of a disease or medical condition (such as COPD) in a patient such as a mammal (particularly a human) that includes: (a) preventing the disease or medical condition from occurring, that is, prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating COPD" would include preventing COPD from occurring, ameliorating COPD, suppressing COPD, and alleviating the symptoms of COPD. The term "patient" is intended to include those mammals, such as humans, that are in need of treatment or disease prevention or that are presently being treated for disease prevention or treatment of a specific disease or medical condition. The term "patient" also includes test subjects in which compounds of the invention are being evaluated or test subjects being used in a assay, for example an animal model.

Synthesis

The crystalline freebase forms of the invention can be synthesized from readily available starting materials as described below and in the Examples. While there may be several methods that can be used to produce each crystalline freebase form, it is noted, however, that the crystalline content as well as the habit of the crystals (size and shape) may vary, based partly upon the method of preparation, as well as on the solvent composition.

It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 25° C. to about 50° C. In other instances, reactions or crystallizations were conducted at room temperature and the temperature was actually measured and recorded. All weights, volumes and equivalents are relative to the biphenyl-2-ylcarbamic acid 1-(2-{[4-(4-carbamoylpiperidin-1-ylmethyl)benzoyl] methylamino}ethyl)piperidin-4-yl ester (or salt form) starting material.

Generally, the crystallizations are conducted in a suitable inert diluent or solvent system, examples of which include, but are not limited to, methanol, ethanol, isopropanol, isobutanol, ethyl acetate, acetonitrile, dichloromethane, methyl t-butyl ether, and the like, and mixtures thereof. Upon completion of any of the foregoing crystallizations, the crystalline compounds can be isolated from the reaction mixture by any conventional means such as precipitation, concentration, centrifugation and the like.

The biphenyl-2-ylcarbamic acid 1-(2-{[4-(4-carbamoylpiperidin-1-ylmethyl) benzoyl]methylamino}ethyl)piperidin-4-yl ester, as well as its salts such as the diphosphate salt, employed in the invention can be readily prepared from commercially available starting materials and reagents using the procedures described in the Examples, or using the procedures described in U.S. Patent Publication No. 2005/0203133 to Mammen et al. and U.S. Patent Publication No. 2007/0112027 to Axt et al.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Form III

Form III crystalline freebase of biphenyl-2-ylcarbamic acid 1-(2-{[4-(4-carbamoylpiperidin-1-ylmethyl)benzoyl] methylamino}ethyl)piperidin-4-yl ester can be prepared from the ester or the diphosphate salt of the ester.

In one embodiment, the Form III crystalline freebase is prepared by contacting biphenyl-2-ylcarbamic acid 1-(2-{[4-(4-carbamoylpiperidin-1-ylmethyl)benzoyl]-methylamino}ethyl)piperidin-4-yl ester with acetonitrile. Typically, the ratio of milligrams of the ester to total milliliters of acetonitrile is about 100:1, with the acetonitrile being added in two steps. Generally, this reaction is conducted while repeatedly cycling through a temperature range of 0-40° C. The solids are then isolated by vacuum filtration and dried.

In another embodiment, the Form III crystalline freebase is prepared using a seed crystal of the Form III crystalline freebase and the diphosphate salt of the ester. This method involves: a) forming a seed crystal of the crystalline freebase Form III; b) dissolving the diphosphate salt of biphenyl-2-ylcarbamic acid 1-(2-{[4-(4-carbamoylpiperidin-1-ylmethyl)benzoyl]methylamino}ethyl)piperidin-4-yl ester in isopropyl acetate and water to form a solution; c) and adding the seed crystal to the solution. More specifically, the diphosphate salt of the ester (1 wt) is slurried in isopropyl acetate (17.5 vol) and water (10 vol) at 20±3° C. under nitrogen. The suspension is warmed to 53±3° C. and 10M NaOH (0.5 vol) is added. The mixture is stirred at that temperature for a short time, then the layers are separated and the basic aqueous layer is removed. Water (5 vol) is added to the organic layer, and stirred. The layers are separated and the water layer is removed. Isopropyl acetate (17.5 vol) is added and about 10 volumes of distillate are collected by atmospheric distillation. This step is repeated with additional isopropyl acetate (10 vol). After the second distillation, the temperature of the clear solution is reduced to 53±3° C., then seeded with a suspension of crystalline freebase Form III (0.005 wt; 0.5 wt %) in isopropyl acetate (0.08 vol). The resulting suspension is stirred at 53±3° C. for at least 2 hours, then cooled to 10±3° C. at an approximate cooling rate of 0.19° C./min. The suspension is stirred at 10±3° C. for at least 2 hours and then is collected by filtration. The resulting filter cake is washed with isopropyl acetate (2×3 volumes) and the product is then dried to yield the Form III crystalline freebase.

Form IV

In one embodiment, the Form IV crystalline freebase is prepared using a seed crystal of the Form III crystalline freebase. This method involves: a) forming a seed crystal of the crystalline freebase Form III; b) dissolving the crystalline freebase Form III in acetonitrile to form a solution; c) and adding the seed crystal to the solution. Typically, the weight ratio of seed to ester is in the range of about 2:250. Typically, the ratio of grams of crystalline freebase Form III to total milliliters of acetonitrile is within the range of about 2:10 to 3:30, with 2.5:16 being one range. The acetonitrile is usually added in several aliquots. Generally, this reaction is conducted while repeatedly cycling through a temperature range of 0-40° C. The solids are then isolated by vacuum filtration and dried.

Crystalline Properties

As is well known in the field of powder x-ray diffraction, relative peak heights of powder x-ray diffraction (PXRD) spectra are dependent on a number of factors relating to sample preparation and instrument geometry, while peak positions are relatively insensitive to experimental details. PXRD patterns for the crystalline freebase Form III and Form IV were obtained as set forth in Example 5. Thus, in one embodiment, a crystalline compound of the invention is characterized by a PXRD pattern having certain peak positions.

Each crystalline freebase form of the invention exhibits a different PXRD pattern, but with certain common peaks. Thus, in one embodiment, the invention relates to crystalline freebase forms of biphenyl-2-ylcarbamic acid 1-(2-{[4-(4-carbamoylpiperidin-1-ylmethyl)benzoyl]methylamino}ethyl) piperidin-4-yl ester characterized by a powder x-ray diffraction pattern comprising diffraction peaks at 2θ values selected from 6.6±0.1, 13.1±0.1, 18.6±0.1, 19.7±0.1, and 20.2±0.1.

In one embodiment, the crystalline freebase Form III is characterized by a powder x-ray diffraction pattern comprising diffraction peaks at 2θ values of 6.6±0.1, 13.1±0.1, 18.6±0.1, 19.7±0.1, and 20.2±0.1; and further characterized by having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1. In another embodiment, the crystalline freebase Form III is characterized by a powder x-ray diffraction comprising diffraction peaks at 2θ values selected from 6.6±0.1, 11.4±0.1, 13.1±0.1, 16.1±0.1, 17.5±0.1, 18.2±0.1, 18.6±0.1, 19.3±0.1, 19.7±0.1, 19.9±0.1, 20.2±0.1, 20.8±0.1, 21.1±0.1, 21.7±0.1, and 22.3±0.1. In yet another embodiment, the crystalline freebase Form III is characterized by a PXRD pattern in which the peak positions are substantially in accordance with those shown in FIG. 1.

In one embodiment, the crystalline freebase Form IV is characterized by a powder x-ray diffraction pattern comprising diffraction peaks at 2θ values of 6.6±0.1, 13.1±0.1, 18.6±0.1, 19.7±0.1, and 20.2±0.1; and further characterized by having five or more additional diffraction peaks at 2θ values selected from 10.6±0.1, 15.0±0.1, 16.0±0.1, 17.3±0.1, 17.7±0.1, 20.9±0.1, 21.4±0.1, 22.6±0.1, 24.6±0.1, and 27.8±0.1. In another embodiment, the crystalline freebase Form IV is characterized by a powder x-ray diffraction pattern comprising diffraction peaks at 2θ values selected from 6.6±0.1, 13.1±0.1, 15.0±0.1, 17.3±0.1, 17.7±0.1, 18.6±0.1, 19.7±0.1, 20.2±0.1, 20.9±0.1, 21.4±0.1, and 22.6±0.1. In yet another embodiment, the crystalline freebase Form IV is characterized by a PXRD pattern in which the peak positions are substantially in accordance with those shown in FIG. 2.

Figure 4:
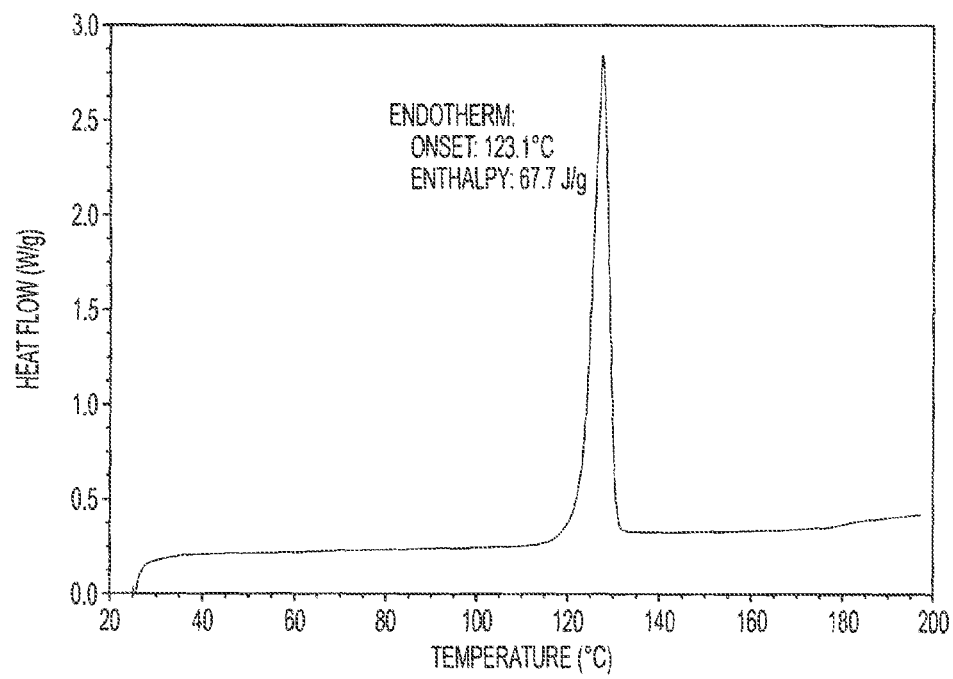
Figure 5:
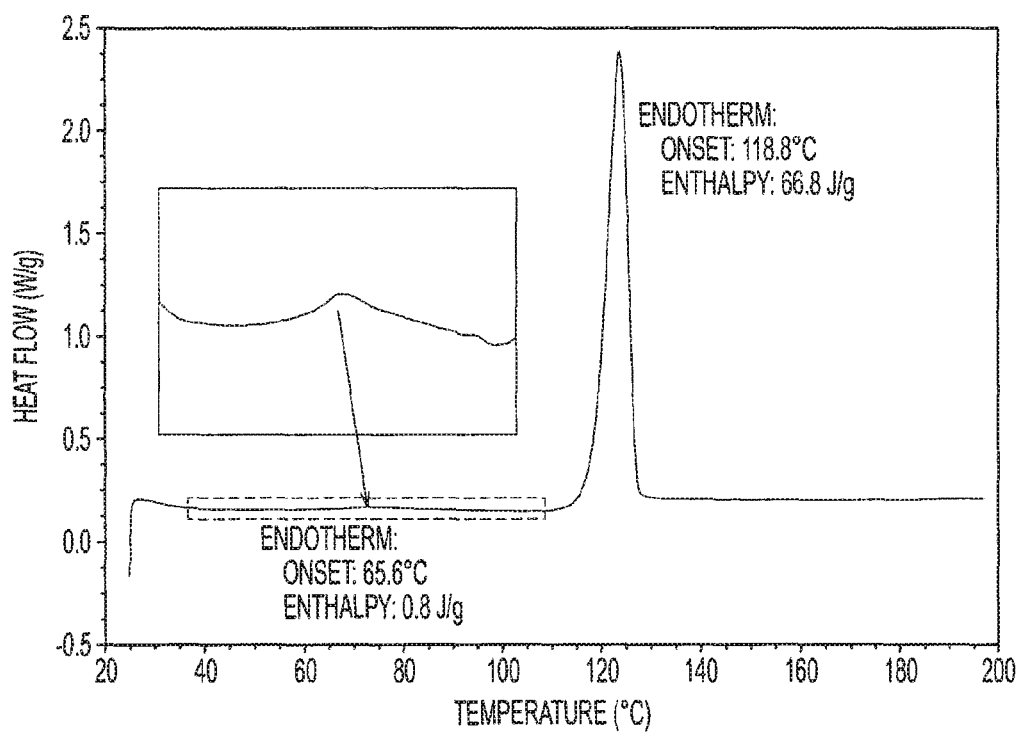

In yet another embodiment, a crystalline freebase of the invention is characterized by a differential scanning calorimetry (DSC) thermogram. DSC thermograms were obtained as set forth in Example 6. Melting points reported herein are estimated on the basis of the melt onset registered during DSC analysis. Thus, in one embodiment, a crystalline compound of the invention is characterized by its DSC thermograph. In one embodiment, the crystalline freebase Form III is characterized by a DSC thermograph which shows an onset of endothermic heat flow at about 123° C. and a melting point of about 125° C., as seen in FIG. 4. In another embodiment, the crystalline freebase Form IV is characterized by a DSC thermograph which shows one onset of endothermic heat flow at about 66° C., a second onset of endothermic heat flow at about 119° C., and a melting point of about 119° C., as seen in FIG. 5.

Thermogravimetric analysis (TGA) was performed on the crystalline freebase forms of the invention as described in Example 6. Thus, in one embodiment, a crystalline freebase is characterized by its TGA trace. In one embodiment, the crystalline freebase Form III is characterized by the TGA trace depicted in FIG. 6. In another embodiment, the crystalline freebase Form IV is characterized by the TGA trace depicted in FIG. 7.

A gravimetric vapor sorption (GVS) assessment was performed on the crystalline freebase forms of the invention as described in Example 7. The crystalline freebase forms of the invention have been demonstrated to have a reversible sorption/desorption profiles with acceptable levels of hygroscopicity. For example, the crystalline freebase Form III showed a reversible water uptake of <2% wt/wt between 0 and 90% relative humidity at 25° C. Additionally, the crystalline freebase Form III has been found to be stable upon exposure to elevated temperature and humidity.

These properties of the crystalline freebase forms of the invention are further illustrated in the Examples below.

Utility

The compound of formula I possesses muscarinic receptor antagonist activity and therefore, a crystalline freebase form of the compound of formula I is expected to be useful for treating medical conditions mediated by muscarinic receptors, i.e., medical conditions that are ameliorated by treatment with a muscarinic receptor antagonist. Such medical conditions include, by way of example, pulmonary disorders or diseases including those associated with reversible airway obstruction such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders such as overactive bladder or detrusor hyperactivity and their symptoms; gastrointestinal tract disorders such as irritable bowel syndrome, diverticular disease, achalasia, gastrointestinal hypermotility disorders and diarrhea; cardiac arrhythmias such as sinus bradycardia; Parkinson's disease; cognitive disorders such as Alzheimer's disease; dismenorrhea; and the like.

Accordingly, in one embodiment, the invention relates to a method for treating a pulmonary disorder, the method comprising administering to a patient a therapeutically effective amount of a crystalline freebase of biphenyl-2-ylcarbamic acid 1-(2-{[4-(4-carbamoyl piperidin-1-ylmethyl)benzoyl]methylamino}ethyl)piperidin-4-yl ester. When used to treat a pulmonary disorder, a crystalline freebase of the invention will typically be administered by inhalation in multiple doses per day, in a single daily dose or a single weekly dose. Generally, the dose for treating a pulmonary disorder will range from about 10 µg/day to 200 µg/day.

When administered by inhalation, a crystalline freebase of the invention typically will have the effect of producing bronchodilation. Accordingly, in another embodiment, the invention relates to a method of producing bronchodilation in a patient, the method comprising administering to a patient a bronchodilation-producing amount of a crystalline freebase of biphenyl-2-ylcarbamic acid 1-(2-{[4-(4-carbamoylpiperidin-1-ylmethyl)benzoyl]methylamino}ethyl)piperidin-4-yl ester. Generally, the therapeutically effective dose for producing bronchodilation will range from about 10 µg/day to 200 µg/day.

In one embodiment, the invention relates to a method of treating chronic obstructive pulmonary disease or asthma, the method comprising administering to a patient a therapeutically effective amount of a crystalline freebase of biphenyl-2-ylcarbamic acid 1-(2-{[4-(4-carbamoylpiperidin-1-ylmethyl)benzoyl]methylamino}ethyl)piperidin-4-yl ester. When used to treat a COPD or asthma, a crystalline freebase of the invention will typically be administered by inhalation in multiple doses per day or in a single daily dose. Generally, the dose for treating COPD or asthma will range from about 10 µg/day to 200 µg/day. As used herein, COPD includes chronic obstructive bronchitis and emphysema (see, for example, Barnes, Chronic Obstructive Pulmonary Disease, *New England Journal of Medicine* 343:269-78 (2000)).

When used to treat a pulmonary disorder, a crystalline freebase of the invention is optionally administered in combination with other therapeutic agents. Accordingly, in a particular embodiment, the pharmaceutical compositions and methods of the invention further comprise a therapeutically effective amount of a $\beta_2$-adrenoreceptor agonist, a corticosteroid, a non-steroidal anti-inflammatory agent, or combination thereof.

In another embodiment, a crystalline freebase of the invention is used to antagonize a muscarinic receptor in biological system, and a mammal in particular such as mice, rats, guinea pigs, rabbits, dogs, pigs, humans and so forth. In this embodiment, a therapeutically effective amount of a crystalline freebase of the invention is administered to the mammal. If desired, the effects of antagonizing the muscarinic receptor can then determined using conventional procedures and equipment.

The properties and utility of a crystalline freebase of the invention, such as the muscarinic receptor antagonizing activity, can be demonstrated using various in vitro and in vivo assays that are well-known to those skilled in the art. For example, representative assays are described in further detail in the following Examples and include by way of illustration and not limitation, assays that measure $hM_1$, $hM_2$, $hM_3$, $hM_4$, and $hM_5$ muscarinic receptor binding (for example, as described in Assay 1). Useful functional assays to determine the muscarinic receptor antagonizing activity of a crystalline freebase of the invention include by way of illustration and not limitation, assays that measure ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio)triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.), and the like. Exemplary assays are described in Assay 2. The crystalline freebase is expected to antagonize or decrease the activation of muscarinic receptors in any of the assays listed above, or assays of a similar nature, and will typically be used in these studies at a concentration ranging from about 0.1-100 nanomolar. Thus, the aforementioned assays are useful in determining the therapeutic utility, for example, the bronchodilating activity, of a crystalline freebase of the invention.

Other properties and utilities of a crystalline freebase of the invention can be demonstrated using various in vitro and in vivo assays well-known to those skilled in the art. For example, the in vivo potency of a crystalline freebase can be measured in an animal model such as the Einthoven model. Briefly, the bronchodilator activity of a crystalline freebase is evaluated in an anesthetized animal (the Einthoven model), which uses ventilation pressure as a surrogate measure of airway resistance. See, for example, Einthoven (1892) *Pfugers Arch.* 51:367-445; and Mohammed et al. (2000) *Pulm Pharmacol Ther.* 13(6):287-92, as well as Assay 3 which describes a rat Einthoven model. Another useful in vivo assay is the rat antisialagogue assay (for example, as described in Assay 4).

Pharmaceutical Compositions and Formulations

A crystalline freebase of the invention is typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. However, it will be understood by those skilled in the art that, once a crystalline freebase of the invention has been formulated, it may no longer be in crystalline form, i.e., the crystalline freebase may be dissolved in a suitable carrier.

Accordingly, in one embodiment, the invention relates to a pharmaceutical composition comprising a pharmaceutically acceptable carrier or excipient and a crystalline freebase of biphenyl-2-ylcarbamic acid 1-(2-{[4-(4-carbamoylpiperidin-1-ylmethyl)benzoyl]methylamino}ethyl)piperidin-4-yl ester. The pharmaceutical composition may contain other therapeutic and/or formulating agents if desired.

The pharmaceutical compositions of the invention typically contain a therapeutically effective amount of a crystalline freebase of biphenyl-2-ylcarbamic acid 1-(2-{[4-(4-carbamoylpiperidin-1-ylmethyl)benzoyl]methylamino}ethyl)piperidin-4-yl ester, as the active agent. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of the invention. The choice of a particular carrier or excipient, or combination of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials that can serve as pharmaceutically acceptable carriers include, but are not limited to, the following: sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; compressed propellant gases such as chlorofluorocarbons and hydrofluorocarbons; and other non-toxic compatible substances employed in pharmaceutical compositions.

The pharmaceutical compositions of the invention are typically prepared by thoroughly and intimately mixing or blending the crystalline freebase with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of the invention are suitable for inhaled administration. Suitable pharmaceutical compositions for inhaled administration will typically be in the form of an aerosol or a powder. Such compositions are generally administered using well-known delivery devices such as a nebulizer inhaler, a metered-dose inhaler (MDI), a dry powder inhaler (DPI) or a similar delivery device.

In a specific embodiment of the invention, a pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the crystalline freebase active agent is typically dissolved in a suitable carrier to form a solution. Suitable nebulizer devices include the Respimat® Soft Mist™ Inhaler (Boehringer Ingelheim), the AERx® Pulmonary Delivery System (Aradigm Corp.), and the PARI LC Plus Reusable Nebulizer (Pari GmbH).

A representative pharmaceutical composition for use in a nebulizer inhaler comprises an isotonic aqueous solution comprising from about 0.05 μg/mL to about 10 mg/mL of a crystalline freebase of the invention. In one embodiment, the aqueous nebulizer formulation is isotonic. In one embodiment, such a solution has a pH of about 4-6. In a particular embodiment, the aqueous nebulizer formulation is buffered with citrate buffer to a pH of about 5. In another particular embodiment, the aqueous formulation contains from about 0.1 mg/mL to about 1.0 mg/mL free base equivalents of biphenyl-2-ylcarbamic acid 1-(2-{[4-(4-carbamoylpiperidin-1-ylmethyl)benzoyl]methylamino}ethyl) piperidin-4-yl ester.

In another specific embodiment of the invention, the pharmaceutical composition comprising the active agent is administered by inhalation using a DPI. Such DPIs typically administer the active agent as a free-flowing powder that is dispersed in a patient's air-stream during inspiration. In order to achieve a free flowing powder, the crystalline freebase active agent is typically formulated with a suitable excipient such as lactose, starch, mannitol, dextrose, polylactic acid, polylactide-co-glycolide, and combinations thereof. Micronization is a common method of reducing crystal size to that suitable for pulmonary delivery. Typically, a crystalline freebase active agent is micronized and combined with a suitable carrier to form a suspension of micronized particles of respirable size, where "micronized particles" or "micronized form" means at least about 90% of the particles have a diameter of less than about 10 μm. Other methods of reducing particle size may also be used such as fine milling, chopping, crushing, grinding, milling, screening, trituration, pulverization, and so forth, as long as the desired particle size can be obtained.

A representative pharmaceutical composition for use in a DPI comprises dry lactose having a particle size between about 1 μm and about 100 μm and micronized particles of a crystalline freebase of the invention. Such a dry powder formulation can be made, for example, by combining the lactose with the crystalline freebase active agent and then dry blending the components. Alternatively, if desired, the crystalline freebase active agent can be formulated without an excipient. The pharmaceutical composition is then typically loaded into a dry powder dispenser, or into inhalation cartridges or capsules for use with a dry powder delivery device.

Examples of DPI delivery devices include Diskhaler (GlaxoSmithKline, Research Triangle Park, N.C.; see, e.g., U.S. Pat. No. 5,035,237 to Newell et al.); Diskus (GlaxoSmithKline; see, e.g., U.S. Pat. No. 6,378,519 to Davies et al.); Turbuhaler (AstraZeneca, Wilmington, Del.; see, e.g., U.S. Pat. No. 4,524,769 to Wetterlin); Rotahaler (GlaxoSmithKline; see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein. The disclosures of the aforementioned patents are incorporated herein by reference in their entirety.

In yet another specific embodiment of the invention, a pharmaceutical composition comprising a crystalline freebase active agent is administered by inhalation using an MDI, which typically discharges a measured amount of the active agent using compressed propellant gas. Accordingly, pharmaceutical compositions administered using an MDI typically comprise a solution or suspension of the crystalline freebase active agent in a liquefied propellant. Any suitable liquefied propellant may be employed including chlorofluorocarbons such as $CCl_3F$, and hydrofluoroalkanes (HFAs) such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents such as ethanol or pentane, and surfactants such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company, the disclosures of which are incorporated herein by reference in their entirety.

A representative pharmaceutical composition for use in a metered-dose inhaler comprises from about 0.01 to 5% by weight of a freebase crystalline compound of the invention; from about 0 to 20% by weight ethanol; and from about 0 to 5% by weight surfactant; with the remainder being an HFA propellant.

Such compositions are typically prepared by adding chilled or pressurized hydrofluoroalkane to a suitable container containing the crystalline freebase active agent, ethanol (if present) and the surfactant (if present). To prepare a suspension, the crystalline freebase active agent is micronized and then combined with the propellant. The formulation is then loaded into an aerosol canister, which forms a portion of a metered-dose inhaler device. Examples of metered-dose inhaler devices developed specifically for use with HFA propellants are described in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.). The disclosures of the aforementioned patents and publications are incorporated herein by reference in their entirety.

For additional examples of processes of preparing respirable particles, and formulations and devices suitable for inhalation dosing see U.S. Pat. No. 6,268,533 to Gao et al., U.S. Pat. No. 5,983,956 to Trofast; U.S. Pat. No. 5,874,063 to Briggner et al.; and U.S. Pat. No. 6,221,398 to Jakupovic et al.; and WO 99/55319 (Glaxo Group Ltd.) and WO 00/30614 (AstraZeneca AB); the disclosures of which are incorporated herein by reference in their entirety.

In another embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a crystalline freebase of the invention as an active ingredient. The pharmaceutical composition may be packaged in a unit dosage form.

When intended for oral administration in a solid dosage form (i.e., as capsules, tablets, pills and the like), a pharmaceutical composition of the invention will typically comprise a crystalline freebase of the invention as the active ingredient and one or more pharmaceutically acceptable carriers such as sodium citrate or dicalcium phosphate. Optionally or alternatively, such solid dosage forms may also comprise: fillers or extenders such as starches, lactose, sucrose, glucose, mannitol, and/or silicic acid; binders such as carboxymethylcellulose, alginates, gelatin, polyvinyl pyrrolidone, sucrose and/or *acacia*; humectants such as glycerol; disintegrating agents such as agar-agar, calcium carbonate, potato or tapioca starch, alginic acid, certain silicates, and/or sodium carbonate; solution retarding agents such as paraffin; absorption accelerators such as quaternary ammonium compounds; wetting agents such as cetyl alcohol and/or glycerol monostearate; absorbents such as kaolin and/or bentonite clay; lubricants such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically acceptable antioxidants include: water-soluble antioxidants such as ascorbic acid, cysteine hydrochloride, sodium bisulfate, sodium metabisulfate sodium sulfite and the like; oil-soluble antioxidants such as ascorbyl palmitate, butylated hydroxyanisole (BHA), butylated hydroxytoluene (BHT), lecithin, propyl gallate, alpha-tocopherol, and the like; and metal-chelating agents such as citric acid, ethylenediamine tetraacetic acid (EDTA), sorbitol, tartaric acid, phosphoric acid, and the like. Coating agents for tablets, capsules, pills and like, include those used for enteric coatings such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The crystalline freebase active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, oils (especially cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

A crystalline freebase of the invention can also be administered transdermally using known transdermal delivery systems and excipients. For example, the crystalline freebase can be admixed with permeation enhancers such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

A crystalline freebase of the invention can also be co-administered with other therapeutic agents. This combination therapy involves using the crystalline freebase combined with one or more of these secondary agents, either formulated together (e.g., packaged together in a single formulation) or formulated separately (e.g., packaged as separate unit dosage forms). Methods of formulating multiple agents together in the same formulation or in separate unit dosage forms, are well known in the art. The term "unit dosage form" refers to a physically discrete unit suitable for dosing a patient, i.e., each unit containing a predetermined quantity of a compound of the invention calculated to produce the desired therapeutic effect either alone or in combination with one or more additional units. For example, such unit dosage forms may be capsules, tablets, pills, and the like.

The additional therapeutic agent(s) can be selected from other bronchodilators (e.g., $PDE_3$ inhibitors, adenosine 2b modulators and $β_2$ adrenergic receptor agonists); anti-inflammatory agents (e.g., steroidal anti-inflammatory agents such as corticosteroids; non-steroidal anti-inflammatory agents (NSAIDs), and $PDE_4$ inhibitors); other muscarinic receptor antagonists (i.e., antichlolinergic agents); antiinfective agents (e.g., Gram positive and Gram negative antibiotics or antivirals); antihistamines; protease inhibitors; and afferent blockers (e.g., $D_2$ agonists and neurokinin modulators).

One particular embodiment of the invention relates to a composition comprising (a) a pharmaceutically acceptable carrier and a therapeutically effective amount of a crystalline freebase of the invention; and (b) a pharmaceutically acceptable carrier and a therapeutically effective amount of an agent selected from a steroidal anti-inflammatory agent such as a corticosteroid; a $β_2$ adrenergic receptor agonist; a phosphodiesterase-4 inhibitor; or a combination thereof; wherein the crystalline freebase and the agent are formulated together or separately. In another embodiment, (b) is a pharmaceutically acceptable carrier and a therapeutically effective amount of a $β_2$ adrenergic receptor agonist and a steroidal anti-inflammatory agent. The secondary agents can be used in the form of pharmaceutically acceptable salts or solvates, and if appropriate, as optically pure stereoisomers.

Representative $β_2$ adrenergic receptor agonists that can be used in combination with a crystalline freebase of the invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $β_2$ adrenergic receptor agonists that can be used include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds described in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds described in WO 02/070490 (Glaxo Group Ltd.); 3-(4-{[6-({(2R)-2-[3-(formylamino)-4-hydroxyphenyl]-2-hydroxyethyl}amino) hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino) hexyl]oxy}butyl)-benzenesulfonamide, N-(t-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino) hexyl]-oxy}butyl)benzenesulfonamide and related compounds described in WO 02/076933 (Glaxo Group Ltd.); 4-{(1R)-2-[(6-{2-[(2,6-dichlorobenzyl)oxy]ethoxy}hexyl) amino]-1-hydroxyethyl}-2-(hydroxymethyl)phenol and related compounds described in WO 03/024439 (Glaxo Group Ltd.); N-{2-[4-((R)-2-hydroxy-2-phenylethylamino) phenyl]ethyl}-(R)-2-hydroxy-2-(3-formamido-4-hydroxyphenyl)ethylamine and related compounds described in U.S. Pat. No. 6,576,793 to Moran et al.; N-{2-[4-(3-phenyl-4-methoxy phenyl)aminophenyl]ethyl}-(R)-2-hydroxy-2-(8-hydroxy-2(1H)-quinolinon-5-yl) ethylamine and related compounds described in U.S. Pat. No. 6,653,323 to Moran et al.; and pharmaceutically acceptable salts thereof. In a particular embodiment, the $β_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $β_2$-adrenoreceptor agonist will be present in the pharmaceutical composition in a therapeutically effective amount. Typically, the $β_2$-adrenoreceptor agonist will be present in an amount sufficient to provide from about 0.05 μg to 500 μg per dose. The disclosures of the aforementioned patents and publications are incorporated herein by reference in their entirety.

Representative steroidal anti-inflammatory agents that can be used in combination with a crystalline freebase of the invention include, but are not limited to, methyl prednisolone, prednisolone, dexamethasone, fluticasone propionate, 6α,9α-difluoro-17α-[(2-furanyl carbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the composition in a therapeutically effective amount. Typically, the steroidal anti-inflammatory agent will be present in an amount sufficient to provide from about 0.05 μg to 500 μg per dose.

An exemplary combination is a crystalline freebase of the invention, co-administered with salmeterol as the $β_2$ adrenergic receptor agonist, and fluticasone propionate as the steroidal anti-inflammatory agent. Another exemplary combination is a e crystalline freebase of the invention, co-administered with a crystalline monohydrochloride salt of N-{2-[4-((R)-2-hydroxy-2-phenylethylamino)phenyl] ethyl}-(R)-2-hydroxy-2-(3-formamido-4-hydroxyphenyl) ethylamine as the $β_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent. As noted above, these agents can be formulated together or separately.

Other suitable combinations include, for example, other anti-inflammatory agents, e.g., NSAIDs (e.g., sodium cromoglycate, nedocromil sodium, and phosphodiesterase (PDE) inhibitors such as theophylline, PDE4 inhibitors and mixed PDE3/PDE4 inhibitors); leukotriene antagonists (e.g., monteleukast); inhibitors of leukotriene synthesis; iNOS inhibitors; protease inhibitors such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

Representative phosphodiesterase-4 (PDE4) inhibitors or mixed PDE3/PDE4 inhibitors that can be used in combination with a crystalline freebase of the invention include, but are not limited to cis 4-cyano-4-(3-cyclopentyloxy-4-methoxyphenyl) cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds described in WO99/16766 (Kyowa Hakko); K-34 (Kyowa Hakko); V-11294A (Napp); roflumilast (Byk-Gulden); pthalazinone compounds described in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with a crystalline freebase of the invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., H₁-receptor antagonists) that can be used in combination with a crystalline freebase of the invention include, but are not limited to, ethanolamines such as carbinoxamine maleate, clemastine fumarate, diphenylhydramine hydrochloride and dimenhydrinate; ethylenediamines such as pyrilamine amleate, tripelennamine hydrochloride and tripelennamine citrate; alkylamines such as chlorpheniramine and acrivastine; piperazines such as hydroxyzine hydrochloride, hydroxyzine pamoate, cyclizine hydrochloride, cyclizine lactate, meclizine hydrochloride and cetirizine hydrochloride; piperidines such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Unless otherwise indicated, exemplary suitable doses for the other therapeutic agents administered in combination with a crystalline freebase of the invention are in the range of about 0.05 µg/day to 100 mg/day.

The following formulations illustrate representative pharmaceutical compositions of the invention, as well as exemplary methods of preparation. One or more secondary agents can optionally be formulated with a crystalline freebase of the invention (primary active agent). Alternately, the secondary agents(s) can be formulated separately and co-administered with the primary active agent, either simultaneously or sequentially. For example, in one embodiment, a single dry powder formulation can be manufactured to include both the crystalline freebase of the invention and one or more secondary agents. In another embodiment, one formulation is manufactured to contain the crystalline freebase of the invention and separate formulation(s) are manufactured to contain the secondary agent(s). Such dry powder formulations can then be packaged in separate blister packs and administered with a single DPI device.

Exemplary Dry Powder Formulation for Administration by Inhalation 0.2 mg of a crystalline freebase of the invention is micronized and then blended with 25 mg of lactose. The blended mixture is then loaded into a gelatin inhalation cartridge. The contents of the cartridge are administered using a powder inhaler.

Exemplary Dry Powder Formulation for Administration by a Dry Powder Inhaler

A dry powder is prepared having a bulk formulation ratio of micronized crystalline freebase of the invention (active agent) to lactose of 1:200. The powder is packed into a dry powder inhalation device capable of delivering between about 10 µg and 100 µg of active agent per dose.

Exemplary Formulations for Administration by a Metered Dose Inhaler

A suspension containing 5 wt % of a crystalline freebase of the invention (active agent) and 0.1 wt % lecithin is prepared by dispersing 10 g of the crystalline freebase as micronized particles with a mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

Alternately, a suspension containing 5 wt % of a crystalline freebase of the invention, 0.5 wt % lecithin, and 0.5 wt % trehalose is prepared by dispersing 5 g of the crystalline freebase as micronized particles with a mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

Exemplary Aqueous Aerosol Formulation for Administration by Nebulizer

A pharmaceutical composition is prepared by dissolving 0.5 mg of a crystalline freebase of the invention (active agent) in 1 mL of a 0.9% sodium chloride solution acidified with citric acid. The mixture is stirred and sonicated until the active agent is dissolved. The pH of the solution is adjusted to a value in the range of from 3 to 8 (typically about 5) by the slow addition of NaOH.

Exemplary Hard Gelatin Capsule Formulation for Oral Administration

The following ingredients are thoroughly blended and then loaded into a hard gelatin capsule: 250 mg of a crystalline freebase of the invention, 200 mg of lactose (spray-dried), and 10 mg of magnesium stearate, for a total of 460 mg of composition per capsule.

Exemplary Suspension Formulation for Oral Administration

The following ingredients are mixed to form a suspension containing 100 mg of active ingredient per 10 mL of suspension.

| Ingredients | Amount |
| --- | --- |
| a crystalline freebase of the invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum k (Vanderbilt Co.) | 1.0 g |
| flavoring | 0.035 mL |
| colorings | 0.5 mg |
| distilled water | q.s. to 100 mL |

Exemplary Injectable Formulation

The following ingredients are blended and the pH is adjusted to 4±0.5 using 0.5 N HCl or 0.5 N NaOH.

| Ingredients | Amount |
| --- | --- |
| a crystalline freebase of the invention | 0.2 g |
| sodium acetate buffer solution (0.4M) | 2.0 mL |
| HCl (0.5N) or NaOH (0.5N) | q.s. to pH 4 |
| water (distilled, sterile) | q.s. to 20 mL |

EXAMPLES

The following Preparations and Examples are provided to illustrate specific embodiments of the invention. These specific embodiments, however, are not intended to limit the scope of the invention in any way unless specifically indicated. The following abbreviations have the following meanings unless otherwise indicated and any other abbreviations used herein and not defined have their standard meaning:

AC adenylyl cyclase
BSA bovine serum albumin
cAMP 3'-5' cyclic adenosine monophosphate
CHO Chinese hamster ovary
$cM_5$ cloned chimpanzee M5 receptor
DCM dichloromethane
dPBS Dulbecco's phosphate buffered saline
EDTA ethylenediaminetetraacetic acid
EtOAc ethyl acetate
FBS fetal bovine serum
FLIPR fluorometric imaging plate reader
HBSS Hank's buffered salt solution
HEPES 4-(2-hydroxyethyl)-1-piperazineethanesulfonic acid
$hM_1$ cloned human M1 receptor
$hM_2$ cloned human M2 receptor
$hM_3$ cloned human M3 receptor
$hM_4$ cloned human M4 receptor
$hM_5$ cloned human M5 receptor
HOBT N-hydroxybenzotriazole
HPLC high-performance liquid chromatography
MCh methylcholine
MeCN acetonitrile Any other abbreviations used herein but not defined have their standard, generally accepted meaning. Unless noted otherwise, reagents, starting materials and solvents were purchased from commercial suppliers (such as Sigma-Aldrich, Fluka, and the like) and were used without further purification.

Preparation 1

Biphenyl-2-ylcarbamic acid 1-(2-{[4-(4-carbamoylpiperidin-1-ylmethyl)benzoyl]methylamino}ethyl)piperidin-4-yl Ester The diphosphate salt of biphenyl-2-ylcarbamic acid 1-(2-{[4-(4-carbamoylpiperidin-1-ylmethyl)benzoyl]methylamino}ethyl)piperidin-4-yl ester (16 g) was dissolved in a biphasic mixture of water (100 mL) and EtOAc (200 mL). NaOH (2 N, 75 mL) was added over a period of 5 minutes. The mixture was then stirred for 30 minutes. The phases were separated and the aqueous phase was extracted with EtOAc (200 mL). The combined organic phases were concentrated. DCM (100 mL) was added, and the mixture evaporated to dryness. The solids were dried in an oven for about 48 hours to yield the title compound (9.6 g).

Example 1

Crystalline Freebase of Biphenyl-2-ylcarbamic Acid 1-(2-{[4-(4-Carbamoylpiperidin-1-ylmethyl)benzoyl]methylamino}ethyl)piperidin-4-yl Ester (Form III)

Biphenyl-2-ylcarbamic acid 1-(2-{[4-(4-carbamoylpiperidin-1-ylmethyl)benzoyl]methylamino}ethyl)piperidin-4-yl ester (102.4 mg) was dissolved in MeCN (500 µL). The solution was stirred at room temperature for 80 minutes and a white solid precipitate formed. The mixture was placed in the shaker block to thermocycle (0-40° C. in one hour blocks) for 48 hours. A white, dense, immobile solid was observed. MeCN (500 µL) was added to mobilize the slurry. The mixture was then placed back in the shaker block for 2 hours. The solids were isolated by vacuum filtration using a sinter funnel, then placed in the piston dryer at 40° C. under full vacuum for 15.5 hours, to yield 76.85 mg of the title crystalline compound.

Example 2

Crystalline Freebase of Biphenyl-2-ylcarbamic Acid 1-(2-{[4-(4-Carbamoylpiperidin-1-ylmethyl)benzoyl]methylamino}ethyl)piperidin-4-yl Ester (Form III)

Diphosphate salt of biphenyl-2-ylcarbamic acid 1-(2-{[4-(4-carbamoyl-piperidin-1-ylmethyl)benzoyl]methylamino}ethyl)piperidin-4-yl ester ($C_{35}H_{43}N_5O_4.2H_3PO_4$; MW 793.75; 632.9 g) was slurried in isopropyl acetate (11.08 L) and water (6.33 L) at room temperature under nitrogen. The suspension was warmed to 53±3° C. and 10M NaOH (317 mL) was added to the stirred mixture, while maintaining the temperature of the mixture above 50° C. The mixture was stirred for approximately 5 minutes at 53±3° C. before allowing the layers to settle. The layers were then separated and the aqueous layer was removed. Water (3.16 L) was added to the organic layer while maintaining the temperature of the mixture above 50° C. The mixture was stirred for 5 minutes at 53±3° C. before allowing the layers to settle. The layers were separated and the water layer was removed. Isopropyl acetate (6.33 L) was added and then about 10 volumes of distillate were collected by atmospheric distillation. This step was repeated with additional isopropyl acetate (3.2 L). After the second distillation, the temperature of the clear solution was reduced to 53±3° C., then seeded with a suspension of the biphenyl-2-ylcarbamic acid 1-(2-{[4-(4-carbamoylpiperidin-1-ylmethyl)benzoyl]methylamino}ethyl)piperidin-4-yl ester crystalline freebase (Form III; 3.2 g) in isopropyl acetate (51 mL). The resulting suspension was stirred at 53±3° C. for 2 hours, then cooled to 10±3° C. over 4 hours. The suspension was stirred at 10±3° C. for at least 2 hours and then the solids were collected by filtration. The resulting filter cake was washed with isopropyl acetate (2×1.9 L) and the product was dried in vacuo at 50° C. to yield the title crystalline compound ($C_{35}H_{43}N_5O_4$; MW 597.76; 382.5 g, 80.3% yield).

Example 3

Recrystallization of Crystalline Freebase of Biphenyl-2-ylcarbamic Acid 1-(2-{[4-(4-Carbamoylpiperidin-1-ylmethyl)benzoyl]methylamino}ethyl)piperidin-4-yl Ester (Form III)

Crystalline freebase of biphenyl-2-ylcarbamic acid 1-(2-{[4-(4-carbamoylpiperidin-1-ylmethyl)benzoyl]methylamino}ethyl)piperidin-4-yl ester (Form III; $C_{35}H_{43}N_5O_4$; MW 597.76; 372.5 g) was slurried in toluene (5.6 L) at 20±3° C. under nitrogen. The suspension was warmed to 82±3° C., and held at this temperature until complete dissolution was observed. The solution was then clarified into the crystallizer vessel, followed by rinsing with toluene (373 µL). Solids were observed in the crystallizer vessel, and the vessel was re-heated to 82±3° C. to effect dissolution, then cooled to 58±3° C. and seeded with a pre-sonicated (approximately 1 minute) of crystalline freebase (Form III; 1.9 g) in toluene (8 µL). The resulting suspension was allowed to stand at 58±3° C. for at least 4 hours, then cooled to 20±3° C. over 2 hours (approximate cooling rate of 0.33° C./min). The suspension was stirred at 20±3° C. for at least 1 hour, then the solids were collected by filtration. The resulting filter cake was washed with toluene (2×1.2 L) and the product was dried in vacuo at 52±3° C. to yield the title crystalline compound (345.3 g, 92.7% yield).

Example 4

Crystalline Freebase of Biphenyl-2-ylcarbamic Acid 1-(2-{[4-(4-Carbamoylpiperidin-1-ylmethyl)benzoyl]methylamino}ethyl)piperidin-4-yl Ester (Form IV)

Biphenyl-2-ylcarbamic acid 1-(2-{[4-(4-carbamoylpiperidin-1-ylmethyl)benzoyl]methylamino}ethyl)piperidin-4-yl ester (prepared as described in Preparation 1; 2.5 g) was dissolved in MeCN (10 mL) to yield a viscous oily pale yellow material. Additional MeCN (5 mL) was added to dilute the material. The solution was seeded with crystalline freebase (20 mg; Form III prepared as described in Example 1) and stirred at room temperature for 90 minutes. A large amount of white precipitate (small crystals) was observed. The slurry was analyzed under a polarized light microscope and found to be birefringent.

Additional MeCN (3 mL) was added and the slurry was placed in a Metz Syn10 block to thermocycle (0-40° C. in one hour blocks) at 800 rpm overnight. The Metz Syn10 is a 10 position parallel reaction station that is static. Agitation of the solution/slurry was by a cross magnetic stirrer bar. The shaker block was a separate piece of equipment that was heated and cooled by an external Julabo bath. The material was removed at 0° C. It was observed that the slurry had settled out, leaving a pale yellow solution above the white precipitate. The slurry was stirred and placed back in the shaker block to thermocycle. The material was removed at 40° C., and stirred at a high agitation rate at room temperature for 80 minutes. The slurry was again analyzed and found to be birefringent. The filter cake was isolated by vacuum filtration using a sinter funnel. MeCN (3 mL) was used to wet the filter paper and the filter cake was washed with MeCN prior to filtration. The cake was deliquored under vacuum for 40 minutes to yield 2.3 g of a flowing white powder. The material was placed in a piston dryer at 40° C. for 65 hours, to yield 2.2 g of the title crystalline compound as a white powder (99.6% purity).

The majority of the Raman spectra of the product was consistent with that of the Form III starting material. However, three shifts were noted:

| Form III | Product |
|---|---|
| 878 cm$^{-1}$ | 881 cm$^{-1}$ |
| 775 cm$^{-1}$ | 772 cm$^{-1}$ |
| 485 cm$^{-1}$ | 488 cm$^{-1}$ |

The product was then analyzed by powder X-ray diffraction, differential scanning calorimetry, and thermal gravimetric analysis. It was determined that the product was a different freebase crystalline from than the Form III starting material, and was designated Form IV.

Example 5

Powder X-Ray Diffraction

Powder X-ray diffraction (PXRD) patterns of the crystalline freebase Forms III (from Example 1) and IV (from Example 4) were acquired on a PANalytical X'Pert Pro powder diffractomer, equipped with an XCelerator detector. The acquisition conditions were radiation: Cu Kα; generator tension: 40 kV; generator current: 45 mA; start angle 2.0° 2θ; end angle 40.0° 2θ, step size: 0.0167° 2θ. The time per step was 31.750 seconds. The sample was prepared by mounting a few milligrams of sample on a Silicon wafer (zero background) plate, resulting in a thin layer of powder.

Characteristic peak positions and calculated d-spacings are summarized below, only reporting those peaks with greater than 14% relative intensity. These were calculated from the raw data using Highscore software. The experimental error in the peak positions is approximately ±0.1° 2θ. Relative peak intensities will vary due to preferred orientation.

| Form III | | |
|---|---|---|
| Pos. [°2Th.] | d-spacing [Å] | Rel. Int. [%] |
| 6.6 | 13.5 | 53.8 |
| 8.8 | 10.1 | 14.8 |
| 10.1 | 8.8 | 14.1 |
| 11.4 | 7.8 | 21.7 |
| 11.6 | 7.6 | 14.7 |
| 13.1 | 6.8 | 29.3 |
| 14.8 | 6.0 | 15.2 |
| 15.2 | 5.8 | 15.8 |

-continued

Form III

| Pos. [°2Th.] | d-spacing [Å] | Rel. Int. [%] |
|---|---|---|
| 16.1 | 5.5 | 30.1 |
| 16.4 | 5.4 | 13.9 |
| 16.9 | 5.2 | 13.8 |
| 17.5 | 5.1 | 25.5 |
| 18.2 | 4.9 | 38.4 |
| 18.6 | 4.8 | 23.6 |
| 19.3 | 4.6 | 23.1 |
| 19.7 | 4.5 | 100.0 |
| 19.9 | 4.5 | 73.5 |
| 20.2 | 4.4 | 22.8 |
| 20.8 | 4.3 | 72.7 |
| 21.1 | 4.2 | 51.5 |
| 21.7 | 4.1 | 21.7 |
| 22.3 | 4.0 | 31.0 |

Form IV

| Pos. [°2Th.] | d-spacing [Å] | Rel. Int. [%] |
|---|---|---|
| 6.6 | 13.4 | 27.1 |
| 10.6 | 8.4 | 13.7 |
| 13.1 | 6.8 | 42.0 |
| 15.0 | 5.9 | 58.4 |
| 16.0 | 5.5 | 15.0 |
| 17.3 | 5.1 | 41.2 |
| 17.7 | 5.0 | 45.6 |
| 18.6 | 4.8 | 100.0 |
| 19.7 | 4.5 | 81.2 |
| 20.2 | 4.4 | 29.7 |
| 20.9 | 4.2 | 34.8 |
| 21.4 | 4.1 | 74.8 |
| 22.6 | 3.9 | 34.3 |
| 24.6 | 3.6 | 18.1 |
| 27.8 | 3.2 | 16.1 |

Figure 2:
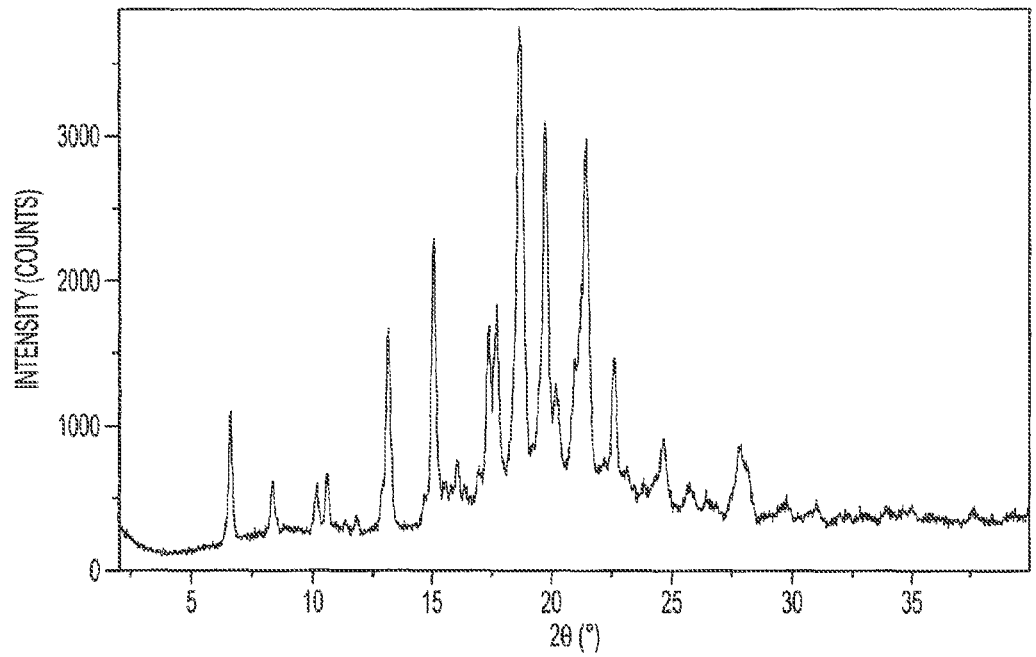
FIG. 2 shows a PXRD pattern of Form IV of the crystalline freebase of the compound of formula I.
Figure 3:
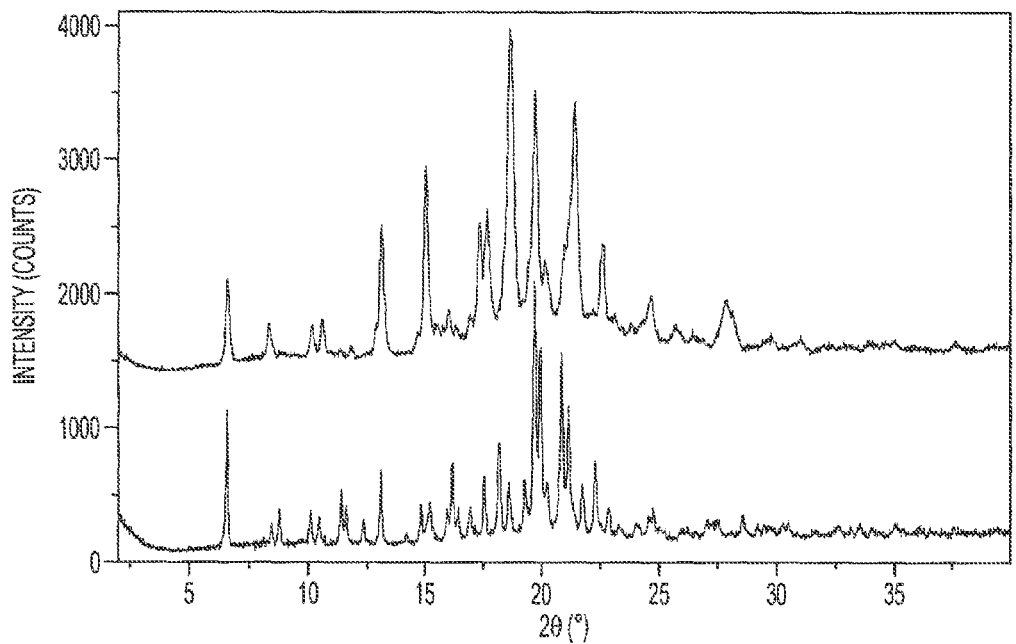
FIG. 3 shows an overlay of the PXRD patterns of Form III and Form IV. Other characteristics of Form IV are presented in FIG. 5, which shows a DSC thermogram, and FIG. 7, which shows a TGA trace.

A representative PXRD pattern for the crystalline freebase Form III is shown in FIG. 1. A representative PXRD pattern for the crystalline freebase Form IV is shown in FIG. 2.

Example 6

Thermal Analysis

Differential scanning calorimetry (DSC) thermograms of the crystalline freebase Forms III (from Example 1) and IV (from Example 4) were obtained using a TA Instruments calorimeter. The samples were weighed into an aluminum pan, a pan lid placed on top and lightly crimped without sealing the pan. The experiments were conducted using a heating rate of 10° C./min.

A representative DSC thermograph for the crystalline freebase Form III is shown in FIG. 4. The DSC thermograph demonstrates that Form III is characterized by a DSC thermograph which shows an onset of endothermic heat flow at 123.1° C. (enthalpy 67.7 J/g).

A representative DSC thermograph for the crystalline freebase Form IV is shown in FIG. 5. The DSC thermograph demonstrates that Form IV is characterized by a DSC thermograph which shows a small endotherm and a main endotherm, i.e., a small first onset of endothermic heat flow occurring at 65.6° C. (enthalpy 0.8 J/g) and a main second onset of endothermic heat flow occurring at 118.8° C. (enthalpy 66.8 J/g).

Thermal gravimetric analysis (TGA) data were obtained using a TA Instruments Q500 instrument. The samples were heated in an open aluminium pan at a heating rate of 10° C./min to 200° C.

Figure 6:
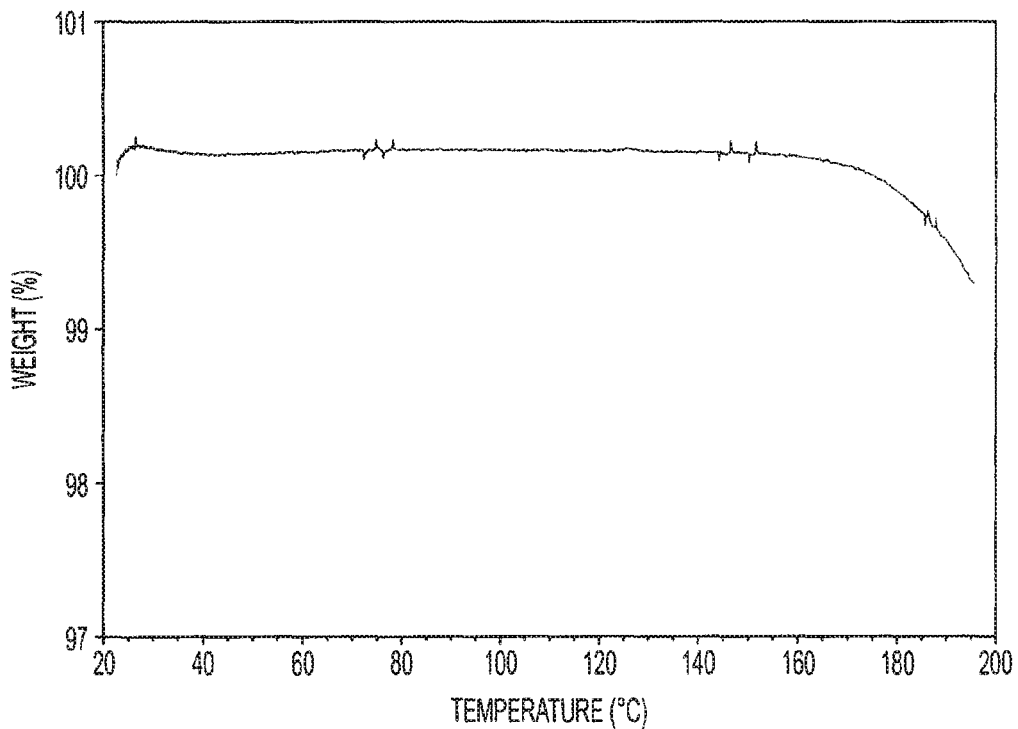
Figure 7:
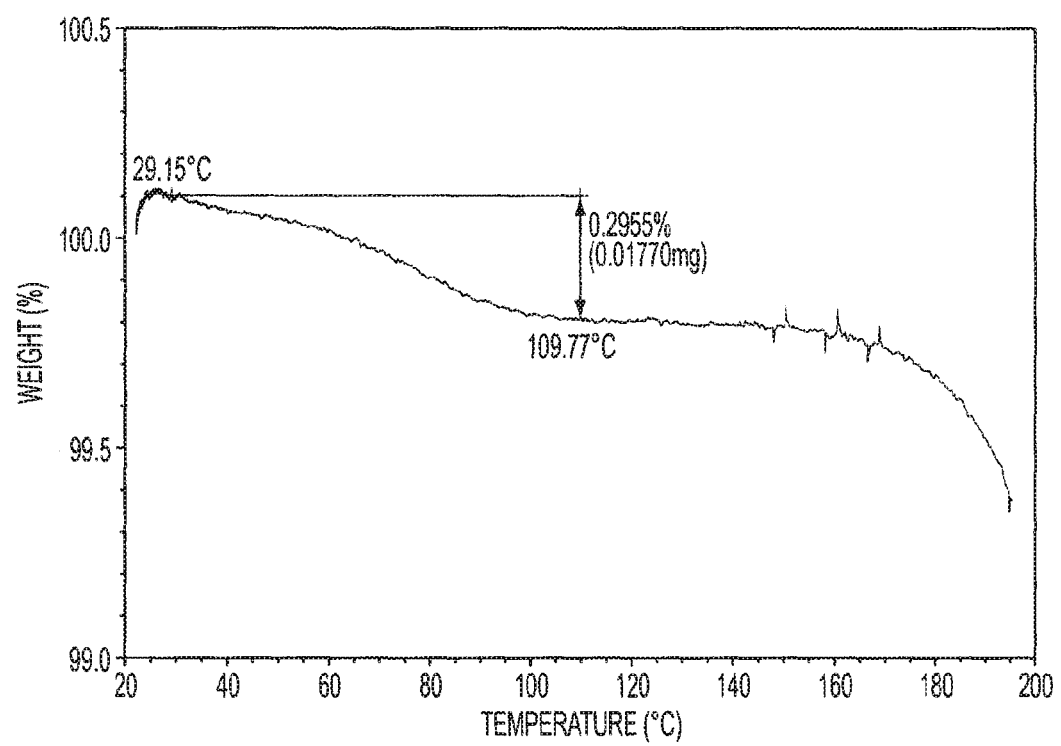

A representative TGA trace for the crystalline freebase Form III is shown in FIG. 6, and indicates that negligible weight loss was observed prior to sample degradation. A representative TGA trace for the crystalline freebase Form IV is shown in FIG. 7, and indicates that approximately 0.3% weight loss was observed prior to sample melt, which is consistent with the loss of residual solvent.

Example 7

Gravimetric Vapor Sorption Assessment

Gravimetric vapor sorption (GVS) studies were performed using a Surface Measurements System DVS-1 instrument for generation of full sorption isotherm using water vapor perfusion at 25° C. A sample size of approximately 7 mg was placed into a clean and dry tared sample mesh pan and weighed using the internal balance. The target relative humidity (RH) ranges were from 30% to 90%, then 90% to 0% and 0% to 30% with 10% steps. The point of equilibrium was automatically determined using a 0.02 dm/dt asymptote setting.

GVS studies on a sample of the crystalline freebase Form III conducted at 25° C. demonstrated that the material had a low propensity to take up moisture over the range 0% RH to 90% RH. The sample showed a reversible water uptake of <2% w/w between 0 and 90% RH at 25° C. This GVS trace demonstrates that Form III has an acceptable weight gain when exposed to a broad humidity range.

Example 8

Micronization

Samples of the crystalline freebase Form III were micronized using either an APTM 4" micronizer and the particle size determined buy laser light diffraction.

| Amt of crystalline material | | Particle size of micronized material (μm) | | |
|---|---|---|---|---|
| input (g) | yield (g) | $X_{10}$ | $X_{50}$ | $X_{90}$ |
| 60.11 | 50.73 | 1.27 | 2.69 | 5.25 |

For reference, the particle size of the input crystalline freebase Form III was $X_{10}$=5.58 μm $X_{50}$=18.2 μm, and $X_{90}$=49.7 μm. Micronization yielded particles in the respirable size range. Micronization resulted in a reduction in crystallinity but retained the essential characteristics of the pre-micronized material. No changes were observed in the PXRD after storage for 3 months at 40° C./20% relative humidity, at 40° C./75% relative humidity (uncapped), and at 50° C./ambient humidity.

The DSC thermograph for the crystalline freebase Form III showed a sharp melt at 125° C., before and after micronization. There was an additional small thermal event in the micronized material at 87° C., likely due to crystallization. After storage for 3 months at 40° C./20% RH, 40° C./75% RH naked, and 50° C./ambient humidity, the micronized material showed a sharp melt at 125° C. with no evidence of amorphous content.

Example 9

Lactose Compatibility

Two formulations of the crystalline freebase Form III were evaluated as to stability for 3 months at 40° C./20% relative humidity (RH), at 40° C./75% RH (uncapped), and at 50° C./ambient humidity. 0.08 wt/wt % (10 µg DPI dose) and 2 wt/wt % (250 µg DPI dose) formulations were prepared as a blend with lactose alone, or with lactose and 1 wt/wt % magnesium stearate. The stability of all formulations was found to be acceptable.

Example 10 pH Solubility and Stability

The crystalline freebase Form III shows good solubility (greater than approximately 2 mg/mL) in media up to pH 7. Solubility in water is 0.66 mg/mL with a natural pH of 8.9. Solubility in simulated lung fluid is 0.46 mg/mL with no change observed between 4 hour and 24 hour solubility measurements.

The crystalline freebase Form III solutions are stable in pH 4 and pH 6 buffers for up to 7 days at 50° C. or exposed to light. The solutions are stable in water and saline for 7 days at room temperature, protected from light.

Assay 1

Radioligand Binding Assay

Membrane Preparation from Cells Expressing $hM_1$, $hM_2$, $hM_3$ and $hM_4$ Muscarinic Receptor Subtypes CHO cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared $hM_5$ receptor membranes were purchased directly from Perkin Elmer and stored at −80° C. until use.

Radioligand Binding Assay on Muscarinic Receptor Subtypes $hM_1$, $hM_2$, $hM_3$, $hM_4$ and $hM_5$ Radioligand binding assays were performed in 96-well microtiter plates in a total assay volume of 1000 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$. The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 40 µM in dilution buffer and then serially diluted 5× with dilution buffer to final concentrations ranging from 400 fM to 4 µM. The addition order and volumes to the assay plates were as follows: 825 µL assay buffer with 0.1% BSA, 25 µL radioligand, 100 µL diluted test compound, and 50 µL membranes. Assay plates were incubated for 6 hours at 37° C. Binding reactions were terminated by rapid filtration over GF/B glass fiber filter plates (Perkin Elmer Inc., Wellesley, Mass.) pre-treated in 0.3% polyethyleneimine (PEI). Filter plates were rinsed three times with wash buffer (10 mM HEPES) to remove unbound radioactivity. Plates were then air dried, and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. The compound of formula I was found to have a $K_i$ value of less than about 5 nM for the $M_3$ muscarinic receptor subtype when tested in this or a similar assay.

ASSAY 2

Muscarinic Receptor Functional Potency Assays

Blockade of Agonist-Mediated Inhibition of cAMP Accumulation

In this assay, the functional potency of a test compound is determined by measuring the ability of the test compound to block oxotremorine-inhibition of forskolin-mediated cAMP accumulation in CHO-K1 cells expressing the $hM_2$ receptor.

cAMP assays are performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells are rinsed once with dPBS and lifted with Trypsin-EDTA solution (0.05% trypsin/0.53 mM EDTA) as described in Assay 1. The detached cells are washed twice by centrifugation at 650×g for five minutes in 50 mLs dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of $1.6 \times 10^6$-$2.8 \times 10^6$ cells/mL.

The test compound is initially dissolved to a concentration of 400 µM in dilution buffer (dPBS supplemented with 1 mg/mL BSA (0.1%)), and then serially diluted with dilution buffer to final molar concentrations ranging from 100 µM to 0.1 nM. Oxotremorine is diluted in a similar manner.

To measure oxotremorine inhibition of AC activity, 25 µL forskolin (25 µM final concentration diluted in dPBS), 25 µL diluted oxotremorine, and 50 µL cells are added to agonist assay wells. To measure the ability of a test compound to block oxotremorine-inhibited AC activity, 25 µL forskolin and oxotremorine (25 µM and 5 µM final concentrations, respectively, diluted in dPBS) 25 µL diluted test compound, and 50 µL cells are added to remaining assay wells.

Reactions are incubated for 10 minutes at 37° C. and stopped by addition of 100 µL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively. The $K_i$ values are converted to $pK_i$ values to determine the geometric mean and 95% confidence intervals. These summary statistics are then converted back to $K_i$ values for data reporting.

In this assay, a lower $K_i$ value indicates that the test compound has a higher functional activity at the receptor tested. The compound of formula I was found to have a $K_i$ value of less than about 5 nM for blockade of oxotremorine-inhibition of forskolin-mediated cAMP accumulation in CHO-K1 cells expressing the $hM_2$ receptor, when tested in this or a similar assay.

Blockade of Agonist-Mediated [$^{35}$S]GTPγS-Binding

In a second functional assay, the functional potency of test compounds can be determined by measuring the ability of the compounds to block oxotremorine-stimulated [$^{35}$S]GTPγS binding in CHO-K1 cells expressing the $hM_2$ receptor.

At the time of use, frozen membranes are thawed and then diluted in assay buffer with a final target tissue concentration of 5-10 µg protein per well. The membranes are briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine is determined in each experiment.

To determine the ability of a test compound to inhibit oxotremorine-stimulated [$^{35}$S]GTPγS binding, the following is added to each well of 96 well plates: 25 µL of assay buffer with [$^{35}$S]GTPγS (0.4 nM), 25 µL of oxotremorine ($EC_{90}$) and GDP (3 µM), 25 µL of diluted test compound and 25 µL CHO cell membranes expressing the $hM_2$ receptor. The assay plates are then incubated at 37° C. for 60 minutes. The assay plates are filtered over 1% BSA-pretreated GF/B filters using a PerkinElmer 96-well harvester. The plates are rinsed with ice-cold wash buffer for 3×3 seconds and then air or vacuum dried. Microscint-20 scintillation liquid (50 µL) is added to each well, and each plate is sealed and radioactivity counted on a topcounter (PerkinElmer). Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. The compound of formula I was found to have a $K_i$ value of less than about 5 nM for blockade of oxotremorine-stimulated [$^{35}$S]GTPγS-binding in CHO-K1 cells expressing the $hM_2$ receptor, when tested in this or a similar assay.

Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leaving 50 µL/well of FLIPR buffer. The cells are then incubated with 50 µL/well of 4 µM FLUO-4AM (a 2× solution was made) for 40 minutes at 37° C., 5% carbon dioxide. Following the dye incubation period, cells are washed two times with FLIPR buffer, leaving a final volume of 50 µL/well.

To determine antagonist potency, the dose-dependent stimulation of intracellular $Ca^{2+}$ release for oxotremorine is first determined so that antagonist potency can later be measured against oxotremorine stimulation at an $EC_{90}$ concentration. Cells are first incubated with compound dilution buffer for 20 minutes, followed by agonist addition, which is performed by the FLIPR. An $EC_{90}$ value for oxotremorine is generated according to the method detailed in the FLIPR measurement and data reduction section below, in conjunction with the formula $EC_F=((F/100-F)^{\wedge}1/H)*EC_{50}$. An oxotremorine concentration of $3 \times EC_F$ is prepared in stimulation plates such that an $EC_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measures the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. The compound of formula I was found to have a $K_i$ value of less than about 5 nM for blockade of agonist-mediated calcium release in CHO cells stably expressing the $hM_3$ receptor, when tested in this or a similar assay.

Assay 3

Rat Einthoven Assay

This in vivo assay is used to assess the bronchoprotective effects of test compounds exhibiting muscarinic receptor antagonist activity. All test compounds are diluted in sterile water and are dosed via the inhalation route (IH). The rats (Sprague-Dawley, male, 250-350 g) are exposed to the aerosol generated from an LC Star Nebulizer Set and driven by a mixture of gases (5% $CO_2$/95% atmospheric air). Each test compound solution is nebulized over a 10 minute time period in a pie shaped dosing chamber capable of holding six rats. At predetermined time points after inhalation of compound, the Einthoven assay is performed.

Thirty minutes prior to the start of pulmonary evaluation, the animals are anesthetized with inactin (thiobutabarbital, 120 mg/kg IP). The jugular vein is catheterized with saline filled polyethylene catheters (PE-50) and used to infuse MCh. The trachea is then dissected and cannulated with a 14G needle and used for rat ventilation during pulmonary evaluation. Once surgery is complete, rats are ventilated using a piston respirator set at a stroke volume of 1 ml/100 g body weight but not exceeding 2.5 ml volume, and at a rate of 90 strokes per minute.

The changes in pressure that occur with each breath are measured. Baseline values are collected for at least 2.5 minutes then rats are challenged non-cumulatively with 2-fold incremental increases of the bronchoconstrictor MCh (5, 10, 20, 40 and 80 µg/ml). The MCh is infused for 2.5 minutes from a syringe pump at a rate of 2 mL/kg/min. The animals are euthanized upon completion of the studies.

Changes in ventilation pressure (cm $H_2O$) in treated animals are expressed as inhibition of MCh response relative to control animals. In this assay, a higher % inhibition value indicates that the test compound has a bronchoprotective effect. The compound of formula I, when tested in this assay at a dose of 100 µg/ml, is expected to exhibit greater than 35% inhibition, possibly greater than 70% inhibition, and even more possibly greater than 90% inhibition.

1.5 hr $ID_{50}$ Determination

Standard muscarinic antagonists were evaluated in the rat Einthoven assay 1.5 hrs post-dose. The order of potency ($ID_{50}$s) for the five standards tested was determined to be: ipratropium (4.4 µg/ml)>tiotropium (6 µg/ml)>des-methyl-tiotropium (12 µg/ml)>glycopyrrolate (15 µg/ml)>LAS-34237 (24 µg/ml). The potency of the test compound is similarly determined at 1.5 hrs post-dose.

6 and 24 hr $ID_{50}$ Determination

Standards tiotropium and ipratropium were also evaluated 24 hr and/or 6 hr post-dose in the rat Einthoven assay. Ipratropium (10 and 30 µg/ml) was about 3-fold less potent 6-hr post-dose compared to its 1.5 hr potency. The observed loss of activity at this time point (6 hr) is consistent with its relatively short duration of action in the clinic. Tiotropium showed a slow onset of effect with peak bronchoprotection being achieved 6-hr post-dose. Its 6 hr and 24 hr potency values were not significantly different from each other and were about 2-fold more potent compared to its 1.5 hr potency. The onset of action of the test compound, as well as the 6 and 24 hr potency values, is similarly determined.

Assay 4

Rat Antisialagogue Assay

Rats (Sprague-Dawley, male, 250-350 g) are dosed, anesthetized and cannulated as described for Assay 3. At predetermined time points and after surgery, animals are placed on their dorsal side at a 20° incline with their head in a downward slope. A pre-weighed gauze pad is inserted in the animal's mouth and the muscarinic agonist pilocarpine (PILO) (3 mg/kg, iv.) is administered. Saliva produced during 10 minutes post-PILO is measured gravimetrically by determining the weight of the gauze pad before and after PILO. Antisialagogue effects are expressed as % inhibition of salivation relative to control animals.

1, 6 and 24 hr $ID_{50}$ Determination

The rat antisialagogue assay was developed to assess systemic exposure and calculate the lung selectivity index (LSI) of test compounds. The standard, tiotropium, was evaluated in this model at 1, 6, and 24 hr post-dose. Tiotropium was found to be most potent at inhibiting pilocarpine-induced salivation 6 hrs post dose. This finding is consistent with the peak effects observed in the Einthoven assay.

This model is a modified version of the procedure described in Rechter, "Estimation of anticholinergic drug effects in mice by antagonism against pilocarpine-induced salivation" *Ata Pharmacol Toxicol* 24:243-254 (1996). The mean weight of saliva in vehicle-treated animals, at each pre-treatment time, is calculated and used to compute % inhibition of salivation, at the corresponding pre-treatment time, at each dose.

Exemplary compounds of the invention that are tested in this assay are expected to exhibit $ID_{50}$ values less than 100 µg/ml (measured at 24 hours), with some compounds expected to exhibit an $ID_{50}$ value less than 30 µg/ml, some less than 20 µg/ml, and some less than 15 µg/ml.

The ratio of the anti-sialagogue $ID_{50}$ to bronchoprotective $ID_{50}$ is used to compute the apparent lung selectivity index of the test compound. Generally, compounds having an apparent lung selectivity index greater than about 5 are preferred.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent

What is claimed is:

1. A pharmaceutical composition comprising a pharmaceutically acceptable propellant and a crystalline freebase of biphenyl-2-ylcarbamic acid 1-(2-{[4-(4-carbamoylpiperidin-1-ylmethyl)benzoyl]methylamino}ethyl)piperidin-4-yl ester characterized by a powder x-ray diffraction pattern comprising diffraction peaks at 2θ values of 6.6±0.1, 13.1±0.1, 18.6±0.1, 19.7±0.1, and 20.2±0.1; and having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1; designated as Form III.

2. The composition of claim 1, wherein the crystalline compound is characterized by a powder x-ray diffraction pattern comprising diffraction peaks at 2θ values selected from 6.6±0.1, 11.4±0.1, 13.1±0.1, 16.1±0.1, 17.5±0.1, 18.2±0.1, 18.6±0.1, 19.3±0.1, 19.7±0.1, 19.9±0.1, 20.2±0.1, 20.8±0.1, 21.1±0.1, 21.7±0.1, and 22.3±0.1.

3. The composition of claim 1, which further comprises an agent selected from $\beta_2$ adrenergic receptor agonists, steroidal anti-inflammatory agents, phosphodiesterase-4 inhibitors, and combinations thereof; wherein the crystalline form and the agent are formulated together or separately.

4. The composition of claim 3, which comprises a $\beta_2$ adrenergic receptor agonist and a steroidal anti-inflammatory agent.

5. The composition of claim 1, wherein the crystalline compound is in a suspension.

6. The composition of claim 1, wherein the propellant is a hydrofluoroalkane.

7. The composition of claim 6, wherein the hydrofluoroalkane is 1,1,1,2-tetrafluoroethane.

8. The composition of claim 6, wherein the hydrofluoroalkane is 1,1,1,2,3,3,3-heptafluoro-n-propane.

9. The composition of claim 1, wherein the composition further comprises a co-solvent selected from ethanol and pentane.

10. The composition of claim 1, wherein the composition further comprises a surfactant selected from the sorbitan trioleate, oleic acid, lecithin, and glycerin.

11. The composition of claim 1, comprising from about 0.01 to 5% by weight of the crystalline compound; from about 0 to 20% by weight ethanol; and from about 0 to 5% by weight surfactant; with the remainder being a hydrofluoroalkane propellant.

12. The composition of claim 1, wherein the crystalline compound is micronized.

13. A pharmaceutical composition comprising 1,1,1,2-tetrafluoroethane and a crystalline freebase of biphenyl-2-ylcarbamic acid 1-(2-{[4-( 4-carbamoylpiperidin-1-ylmethyl)benzoyl]methylamino}ethyl)piperidin-4-yl ester characterized by a powder x-ray diffraction pattern comprising diffraction peaks at 2θ values of 6.6±0.1, 13.1±0.1, 18.6±0.1, 19.7±0.1, and 20.2±0.1; and having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1; designated as Form III.

14. A pharmaceutical composition comprising 1,1,1,2,3,3,3- heptafluoro-n-propane and a crystalline freebase of biphenyl-2-ylcarbamic acid 1-(2-{[4-(4-carbamoylpiperidin-1-ylmethyl)benzoyl]methylamino}ethyl) piperidin-4-yl ester characterized by a powder x-ray diffraction pattern comprising diffraction peaks at 2θ values of 6.6±0.1, 13.1±0.1, 18.6±0.1, 19.7±0.1, and 20.2±0.1; and having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1; designated as Form III.

15. The composition of claim 3, which comprises a $\beta_2$ adrenergic receptor agonist.

16. The composition of claim 3, which comprises a steroidal anti-inflammatory agent.

17. The composition of claim 3, which comprises a phosphodiesterase-4 inhibitor.

* * * * *